United States Patent [19]

Minet et al.

[11] Patent Number: 4,520,217
[45] Date of Patent: May 28, 1985

[54] PYROLYSIS OF NATURAL GAS LIQUIDS TO AROMATIC HYDROCARBONS USING A HOT RECYCLED GAS

[75] Inventors: Ronald G. Minet, Pasadena, Calif.; Mario Dente; Eliseo Ranzi, both of Milan, Italy; Sunny H. K., Pasadena, Calif.

[73] Assignee: Kinetics Technology International Corp., Monrovia, Calif.

[21] Appl. No.: 329,430

[22] Filed: Dec. 10, 1981

[51] Int. Cl.³ .................. C07C 2/54; C10G 35/02
[52] U.S. Cl. .................... 585/415; 208/130; 208/133
[58] Field of Search ............ 585/415; 208/133, 106, 208/130

[56] References Cited

U.S. PATENT DOCUMENTS

| | | | |
|---|---|---|---|
| 1,763,604 | 6/1930 | Harnsberger | 208/106 |
| 2,296,601 | 9/1942 | Dorsett et al. | 208/106 |
| 2,764,622 | 9/1956 | Marisic et al. | 208/106 |
| 3,271,298 | 9/1966 | Dulaney et al. | 208/106 |
| 4,166,025 | 8/1979 | Nametkin et al. | 208/130 |
| 4,256,565 | 3/1981 | Friedman et al. | 208/130 |
| 4,426,278 | 1/1984 | Kosters | 208/130 |
| 4,458,096 | 7/1984 | Phillips et al. | 208/130 |

Primary Examiner—Delbert E. Gantz
Assistant Examiner—Lance Johnson
Attorney, Agent, or Firm—Albert L. Gabriel

[57] ABSTRACT

Method and apparatus for converting components of natural gas liquids to aromatic compounds by certain pyrolysis and recycle steps wherein the ultimate yield of light aromatics is maximized while the compression and other costs are minimized.

4 Claims, 2 Drawing Figures

PYROLYSIS OF NATURAL GAS LIQUIDS TO AROMATIC HYDROCARBONS USING A HOT RECYCLED GAS

BACKGROUND OF THE INVENTION

1. Field of the Invention

The invention is in the field of pyrolysis in tubular furnaces.

2. Description of the Prior Art

Light aromatic hydrocarbons, comprising benzene, toluene, the xylenes, ethylbenzene and styrene, are presently mainly derived from petroleum oil and are the major building blocks for many of the commercially important synthetic resins and plastics. Many of these are also relatively crucial in supplying the octane enhancement necessary in the higher performance gasolines, especially the increasingly important lead-free higher octane gasolines.

In coming years, however, the world supply of the lighter crude oils from which economical yields of these aromatics can be obtained will be diminishing. While the world supply of total crude petroleum oil is expected to increase very slightly (1% per year) over the next one or two decades, the desirable light crude is expected to gradually diminish as it is and has been preferentially utilized.

Meanwhile, relatively abundant amounts of natural gas are being found, especially in places remote from markets. Worldwide natural gas is expected to increase in usage by about 2.2% per annum, and the probable and potential reserves thereof are expected to rival the sum of those of oil shale and tar sands combined. The concomitant supply of the lighter portion of the natural gas liquid fraction—comprising ethane, propane and the butanes—is expected to be in excess supply at some of the more remote locations. This so-called liquified petroleum gas (LPG) is relatively difficult to transport from remote locations, and so it is a candidate for conversion to more easily transportable and more valuable products.

Commercially, LPG is a well-known and widely used raw material for the production of such olefins as ethylene and propylene by pyrolytic means. However, these products are even more difficult and costly to transport than their precursors.

Invariably, in the well-known production of ethylene and propylene from aliphatic hydrocarbons by pyrolysis some aromatic by-products are produced. However, especially with LPG as the precursor raw material, the yield is often so small that, rather than being a fruitful source of these compounds, their production is in nuisance proportions, to be separated from the desired product and quickly disposed of—for example, as furnace fuel.

Much research and development effort has been expended upon pyrolytic means, including much directed towards enhancing the yield of valuable aromatic compounds. It has, for example, been taught by Smith and Boston (U.S. Pat. No. 2,852,440, issued Sept. 16, 1958) under the auspices of Esso Research and Engineering, that by pyrolysis in a first zone at relatively high hydrocarbon partial pressure, e.g., 30–100 psia, and in a second zone at relatively low partial pressure, e.g., 2–20 psia, a higher yield of aromatics is obtained, along with a relatively high yield of unsaturated compounds. However, such a high pressure drop and low offgas partial pressure entails very costly subsequent compression with very large and expensive compressors or very large amounts of increasingly costly dilution steam, and usually both.

Furthermore, the bulk of the aromatic content of the pyrolytic offgas arises in the first relatively high pressure zone, and must pass through the second zone where the bulk of the desired unsaturated products are produced. Aromatics are thus present in relatively high (i.e., as high or higher than product concentrations) in the presence of unsaturates at their full product concentrations. Under such pyrolytic conditions much alkylation of the desired aromatics by the unsaturates will rapidly take place, thus producing relatively large quantities of relatively useless aromatic tar, rather than the most desired lower members, benzene, toluene and xylenes (so-called BTX).

Still further, in order to obtain BT yields of only about 13 weight percent, an inordinately long residence time is required in the first zone, i.e., about three seconds. Such a long residence time would require either inordinately long tubes, or low, inefficient-for-heat-transfer velocities or both.

Even further, Smith and Boston do not contemplate producing aromatics from LPG, but rather from gas oil (preferably boiling between 430° F. and 1000° F.).

It has been long known, of course, that higher molecular weight products, much of it in the gasoline boiling range, can be produced from unsaturated gases. This product has been known as "poly-gasoline", and the typical process used was generally described as in 1935 by C. R. Wagner (Industrial and Engineering Chemistry, Vol. 27, pages 933–936), in which in a commercial unit as much as 25 gallons of such product per 1000 cubic feet of gas were obtained by recycling unsaturates through a zone at 950° F. and 800 psig. This product was of only moderate octane number (ASTM method, 78), indicating only a modest aromatic content.

In parallel research efforts cited by Wagner, however, it was also found that, if the "olefin-bearing gases were heated quickly to 1100° F. or higher and then allowed to rise in temperature because of the exothermic heat of reaction until a final temperature of 1200° F. to 1300° F. was reached, . . . a highly aromatic distillate from which gasoline having an octane number (ASTM) of approximately 100 could be produced." However, no other details of the conditions were given, except a mention (in the abstract) that the pressure was "low", presumably relative to the above-cited 800 psig.

In later experimental work, such as that of Towell and Martin (AICHE Journal, Vol. 1, pages 693–8) reported in Dec., 1961, it was found that in pyrolyzing ethylene at temperatures between about 600° C. and 1200° C. that "hydrogen, 1, 3 butadiene and acetylene were considered to be the major primary products", and that the presence of propylene greatly inhibited the pyrolysis of ethane to ethylene (their FIG. 10).

Fairly recently, in 1969, Kunugi, et al. (I & EC Fundamentals, Vol. 8, pages 374–383) reported a comprehensive study of the thermal reaction of ethylene at temperatures between about 703° C. and 854° C., at initial ethylene partial pressures between about 0.25 and 1 ata (atmospheres absolute), at various residence times between about 0.25 and 2.4 seconds, and with additives including ethane and butadiene. The same laboratory had previously similarly studied the thermal reaction of propylene and butadiene in papers presented to the Chemical Society of Japan and the Japan Petroleum Institute, respectively. Kunugi, et al. concluded that ethane initiated the reactions and that butadiene was a necessary intermediate in the formation of aromatics. However, with either of these additives in the best of their reported results, the yield of BT was only 0.787 and 0.327 (their tables III and IV), mols per 100 mols of feed respectively. Selectivity to benzene was less than about 8.5 mols per 100 mols of ethylene converted.

The same laboratory then reported a comprehensive study (Kunugi, et al., I & EC Fundamentals, Vol. 9, pages 314–324), in 1970, upon the thermal reaction of propylene. Here Kunugi, et al., concluded that the initiator was 1-butene and that the selectivities to the main products are independent of temperatures from 750° C.–850° C. Their results show selectivities to benzene up to about 6 mols per 100 mols propylene converted and less than 3 mols/100 converted for toluene.

Finally, under the auspices of Socony-Vacuum (now Mobil), Kinney and Crowley (Industrial and Engineering Chemistry, Vol. 46, pages 258-64) reported in 1954, a comprehensive laboratory study aimed at maximizing the production of aromatics from refinery gases (including some ethylene and propylene along with the LPG gases), as shown in their Table II. Yield of light aromatics ($C_6$-$C_8$) reported was less than 10.5 weight %. Furthermore, the yield of coke was always appreciable, and in some cases exceeded the yield of these desired aromatics. Such an amount of coke—even at the lowest of coke yields, 2.5 weight %—would be much more than enough to preclude the use of tubular pyrolysis furnaces, since the tubes would very quickly coke up, plug up, and at the process temperatures involved (1500° F.), overheat and burn out rapidly in a fired tubular furnace.

Kinney and Crowley also investigated the yields of light aromatics from the individual gases: ethylene, ethane, propylene and propane, under conditions of maximum aromatic formation. Temperature was 1500° F., residence times were within the range of 3-20 seconds, and the hydrocarbon partial pressure was (presumably) one atmosphere. Results are shown in their Table III, from which selectivities to light aromatics may be calculated as 25.2, 11.5, 14.9 and 10.8 weight percent, respectively. In every case the selectivity to heavy aromatic "tar" exceeded that to the desirable light aromatics, and in some cases approached twice the selectivity to the light aromatics. Their FIG. 8 shows the selectivity to coke, which at these conditions varied from about 2.5 to about 9 weight percent.

The above art is by no means exhaustive, but is representative of the better attempts, as well as of the practical difficulties involved in attempting to commercially utilize tubular furnaces to produce BTX from LPG and the like in relatively high ultimate yields in an economical process. To the present authors' knowledge, there has been no disclosure of a practical means or conditions of so doing. In view of the clear economic incentives both as cited hereinabove and as implied by the persistence over the years represented by the work cited above signifying the numerous attempts to obtain such a practical means, it is clear that discovering and devising such a means is well beyond mere ordinary skill in the art.

SUMMARY OF THE INVENTION

In view of the cited and other problems in the art, it is a general object of the present invention to provide a novel method and apparatus for the more efficient production of light aromatics from natural gas liquid components, wherein such feed components are pyrolyzed in one or more tubular furnaces, with the offgas fraction containing said components and related unsaturates being recycled to further pyrolysis, thereby very substantially increasing the yield of light aromatics.

By substantially completely recycling to further pyrolysis under carefully selected conditions, for example, the two to four carbon atom products of pyrolysis, these components are completely converted to other products, and light aromatics are produced, under preferred conditions, in ultimate yields of over 30 weight percent of the feed hydrocarbons. Ultimate yields in a recycle operation may be properly compared to selectivities in a single pass operation. Thus, this 30 weight percent obtainable with a propane feed according to the present invention compares to a 10.8 weight percent cited above obtained by Kinney and Crowley using propane feed.

Another object of the invention is to pyrolyze one or more components present in natural gas liquids in a tubular furnace and convert the gaseous products therefrom to light aromatics in substantially maximum ultimate yield.

A further object of the invention is to obtain such high ultimate yields of light aromatic products while maximizing the pressure at the final pyrolysis coil outlet, thereby minimizing the costs of subsequent compression of the pyrolysis offgases.

Another object of the invention is to minimize the recycle ratio of, for example, 2 to 4 carbon atom, gases recycled per unit of fresh feed, while obtaining such high ultimate yields, thereby further minimizing the costs of compression.

Another object of the invention is to minimize increasingly costly dilution steam which is commonly utilized in large quantities in commercial tubular pyrolysis furnaces.

Another object of the invention is to minimize the production of relatively low value heavy aromatics.

Another object of the invention is to minimize the production of coke, to the point that commercially adequately long runs before decoking may be made while at the same time converting relatively highly unsaturated recycle streams to aromatics.

According to the invention, high ultimate conversions of aliphatic hydrocarbonaceous feeds to light aromatics by pyrolysis is achieved not by relatively long residence time as taught by the prior art, but by comparatively very short residence times with recycle of at least a portion of the 2 to 4 carbon atom content of the offgases. By such means it has now been found that the ratio of the yield of light aromatics to the yield of heavy aromatics may be increased from the one-half or less of the prior art to, under preferred conditions, 1.5 or more—of course with great effect upon the total ultimate yield of light aromatics.

Also, according to a preferred embodiment of the invention, the $C_2$-$C_4$ recycle gases, rather than being introduced along with fresh feed into the pyrolysis coil of the tubular furnace, are admixed with the pyrolyzed feed in a second hot zone after the pyrolysis in a first zone.

Still further, according to a more preferred embodiment of the invention, said second zone comprises an eductor means utilizing as motive fluid higher pressure recycle gases such that the pressure at the outlet of the first zone is increased in the second zone. This is exactly opposite to the teachings of Smith and Boston and thereby overcomes the numerous disadvantages cited above in respect to their teachings. Thus, instead of the second zone being at a lower pressure than the first, it is at a higher pressure, minimizing subsequent compression costs and so forth. Even more importantly, the maximum light aromatic content of the gases never is in contact with the maximum in unsaturated content, since in the present invention unsaturated content is diminishing as aromatic content builds up. Thus, alkylation to low value heavy aromatics of the latter by the former is minimized.

It is, of course, to be emphasized that the recycle gases are available at such relatively higher pressure without the need of compression thereof. They are present at such higher pressure because of the need in any case in the separation train for such pressures in order that recovery by liquifaction is practically feasible for such relatively low boiling gases. Such availability, therefore, represents "free" motive fluid for the eductor means.

Furthermore, because of the exothermicity of the reaction of unsaturates to aromatics, in the more preferred embodiment it is unnecessary to heat the gases in the second zone, but rather merely insulate it from appreciable heat loss. Thus the tube walls of the eductor are cooler rather than hotter, in contrast to the case of the required high-heat-input flux in pyrolysis coils, such as in the first zone. In this manner, both due to the heat release of the fluid and to the relatively cool walls, temperatures are practically attainable in said second zone which would be unattainable in a fired pyrolysis coil. Such temperatures encourage both more cracking of saturates and more rapid conversion of unsaturates to light aromatics. In consequence, required pyrolysis residence time in said second zone is reduced to less than about one second and, preferably, to less than about 0.5 seconds, and still more preferably to less than about 0.3 seconds.

In the preferred embodiment the coil outlet temperature of the first zone is greater than about 750° C. and usually greater than about 800° C., and the pyrolysis zone residence time therein (i.e., at temperatures greater than about 620° C.) is less than about 1 second, preferably less than about 0.7 seconds, and still more preferably less than about 0.6. Thus the optimum total residence time at pyrolysis temperatures has now been found to be less than about 0.9 seconds, in sharp contrast to the prior art.

While the invention is suited to a variety of hydrocarbon partial pressures in each of the zones, it will generally be preferred that the hydrocarbon partial pressure near the outlet of the first zone be maintained below about 2 atmospheres absolute (ata), and that the pressure near the outlet of the second zone be maintained above about 2 ata. Again this is in sharp contrast to the proposals in the prior art, where normally there would be substantial pressure drop in the second zone, of the order of 0.5 ata.

It is necessary to preheat the recycled fraction of the offgases from the pyrolysis unit in a third zone, preferably above about 800° C., which should preferably take place in an additional fired coil. It has been found that, if the total residence time in this coil is maintained below about 0.5 seconds, preferably below about 0.3 seconds, relatively little reaction takes place in this zone, in spite of unsaturate contents therein in excess of 50%. This is somewhat surprising and not suggested by the prior art. For example, the report of C. R. Wagner cited above would imply that extensive conversion of unsaturates to aromatics should take place about 1200° F., let alone above 800° C. (1472° F.). This finding shows that conditions other than those cited by Wagner are important in this respect. Although it can only be surmised, it may be that the presence of propylene, which is a known inhibitor (e.g., Towell and Martin hereinabove), and the relatively low contents of ethane and 1-butene which are known initiators (e.g., Kunugi et al. hereinabove), accounts for the unexpected relative unreactivity of the recycled stream in the third zone.

In any case, when the recycled $C_2$–$C_4$ gases are admixed in the second zone with the freshly cracked product of the first zone, the mixture becomes reactive and relatively quickly converts to a substantial extent to light aromatics. At the inlet of the second zone reactive initiators present or produced in the first zone react in the second zone. Quite likely such initiators comprise more than ethane and 1-butene and may well include cyclohexene which is not recycled in the preferred embodiment. Cyclohexene is known to pyrolyze to ethylene and butadiene. In addition, the absence of hydrogen itself in the recycle may account for its apparently relatively long induction period, since it is well known that reactions involving both molecular and atomic hydrogen are much, much faster than those involving only hydrocarbons with their radicals.

Further objects and advantages of the present invention will appear during the course of the following part of the specification, wherein the details of the method and apparatus of presently preferred embodiments are described with reference to the accompanying drawings, in which:

DETAILED DESCRIPTION

Figure 1:
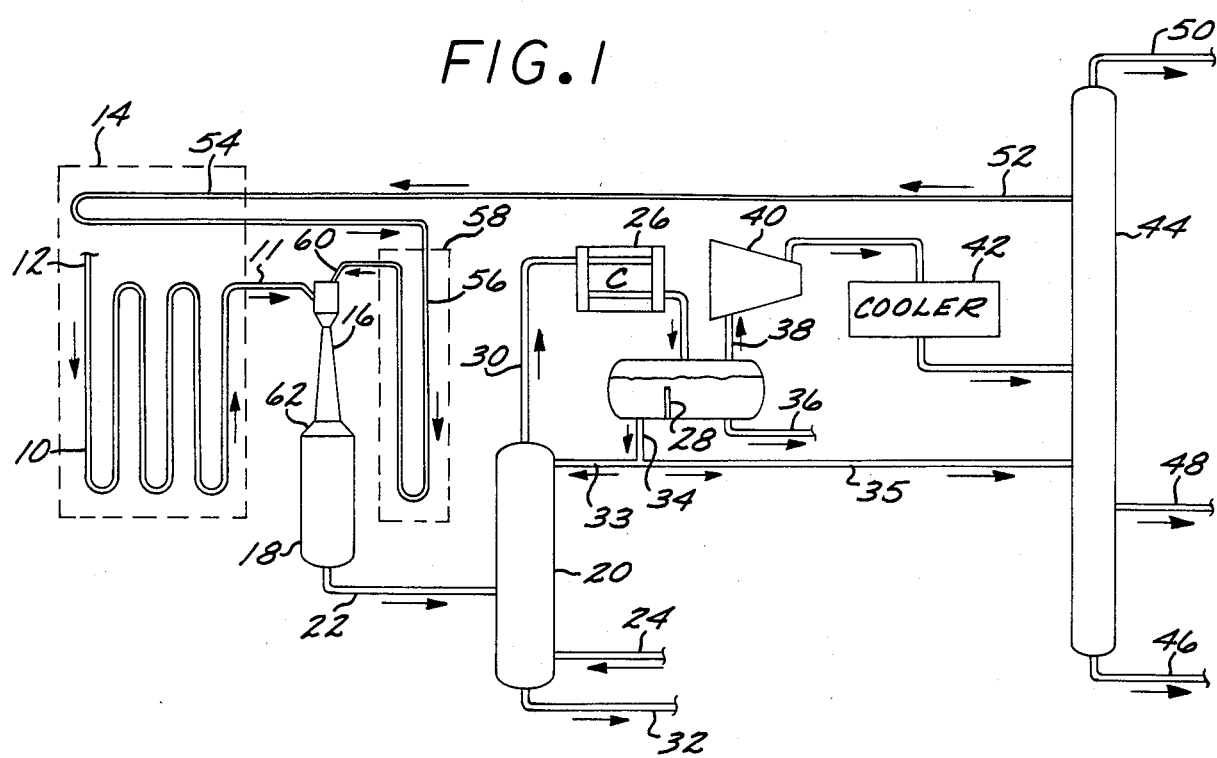
FIG. 1 is a flow diagram of the preferred embodiment of the present process for the production of light aromatics from one or more components of natural gas liquids in accordance with the present invention.

Referring to FIG. 1, fresh feed gas comprising any one or more of: ethane, propane, normal butane and isobutane—preferably admixed with steam as in conventional practice, is introduced to pyrolysis coil 10 in heated enclosure 14 via line 12, preferably under a total pressure between about 2 and 4 ata. Normally, line 12 is connected upstream to a preheat coil (not shown) in the convection section of a furnace, and the temperature in line 12 is in the vicinity of about 620° C., and coil 10 is in the radiant section of a fired furnace.

In the preferred embodiment of the present invention, the outlet of coil 10 connects to the suction of eductor 16 at nozzle 11. It is not necessary to have eductor 16 within heated enclosure 14, but rather merely to insulate it against appreciable heat loss. After passing through eductor 16, the pyrolyzed gases enter quench cooler 18. Cooling therein may either be by indirect contact (as shown), i.e., transferring heat through tubular means to boiling fluid, usually water, and thereby recovering much of the heat present in the pyrolyzed gases usefully in the form of high pressure vapor such as steam to drive compressors; or by direct contact using a quench fluid.

Recovery of the various fractions contained in said gases is by conventional means. Thus, as shown, the effluent from cooler 18 enters fractionator 20, and heavy tar may be taken from the bottom of fractionator 20 via line 32 substantially free of light aromatics by the introduction of stripping steam in line 24. Vapors of light aromatics leave fractionator 20 via line 30 and are condensed in condenser 26, along with water from any steam introduced as dilution steam in line 12 or as stripping steam in line 24. The stream from line 30 then enters separator 28. From separator 28, a hydrocarbonaceous phase is withdrawn via line 34 and split into reflux in line 33 and product in line 35, an aqueous phase via line 36 and a gas phase via line 38, which is then compressed and separated into various cuts and products in a subsequent conventional compression/cooling/fractionation train.

This train is merely symbolized by compressor 40, cooler 42, and fractionator 44. Its precise design is dictated by ordinary skill-in-the art considerations, and, depending upon marketing and transportation considerations, liquid product fractions may be separated from each other or may not. For convenience in showing the yield structure, a total of five fractions are shown: heavier than 8 carbon atom products (tar) in line 32, 6 to 8 carbon atom light aromatics in line 46 (light aromatics), 5 to 8 carbon atom non-aromatics (non-aromatics) in line 48, a hydrogen/methane stream in line 50, and a 2 to 4 carbon atom stream (recycle) in line 52.

The latter stream is recycled, preferably as shown: through convection section preheat coil 54, in which the temperature is preferably increased to about 550° C. (1022° F.), and radiant section coil 56 in heated enclosure 58, in which its temperature is increased to greater than about 750° C. (1382° F.), and preferably greater than about 800° C. (1472° F.). Coils 54 and 56 may be within the same or another, separate, furnace from that utilized to pyrolyze the fresh feed; and, indeed, separate coil 56 may be eliminated and the stream in line 52 may be mixed with that in line 12. However, in the preferred embodiment, as shown in FIG. 1, such is not preferred, but rather the effluent from coil 56, at nozzle 60, serves as the motive fluid for eductor 16.

Thus, preferably, the pressure of the stream at nozzle 60 is greater than about 4 ata but less than about 20 ata, and more preferably at least about 6 ata; and preferably the pressure at exit nozzle 62 from eductor 16 is greater than about 2 ata, and more preferably greater than about 2.5 ata (36.8 psia), thereby minimizing compression costs and maximizing the rate of conversion of olefins to aromatics.

Figure 2:
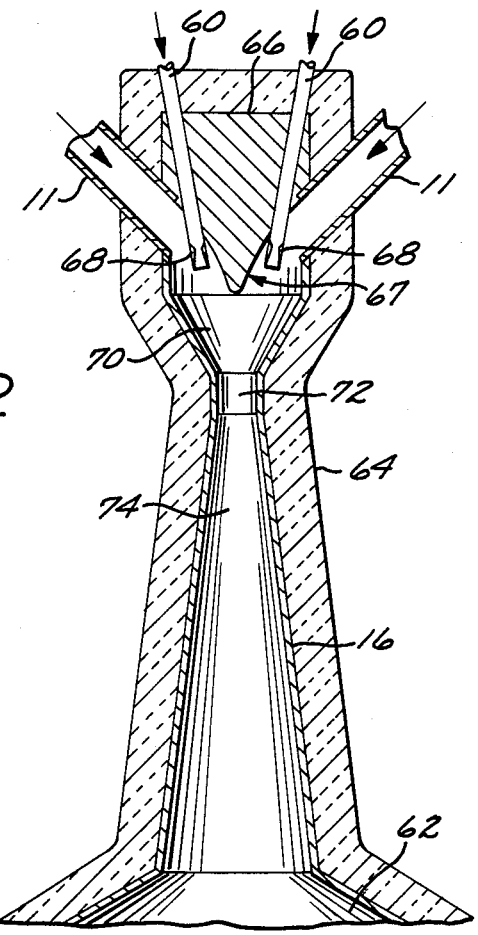
FIG. 2 is an enlarged schematic vertical axial section of the eductor means, comprising the second zone of the preferred embodiment.

Referring to FIG. 2, the eductor 16 is preferably fabricated from high temperature resistant metal alloy and preferably is coated internally to minimize coke laydown and to produce a hard, wear-resistant surface. Such hard and adherent coatings preferably comprise oxides of aluminum and chromium and admixtures thereof. These coatings may be produced by well-known means. Eductor 16 is externally covered with thermal insulating material 64, and it is preferred that it have a center of symmetry, such that entrance nozzles be symmetrical. Thus it is preferred that there be at least two entrance suction nozzles 11, symmetrically opposed to each other and entering in a downstream-facing direction, as shown. In this way, coke buildup in inlet section 66, which will tend to form particularly in dead zones (where residence time tends to be protracted), will actually tend to streamline the internal flow of streams from nozzles 11, somewhat as shown by coke surface 67.

It will thus be preferred that coil 10 of FIG. 1 actually will be two or more (so-called "split") coils, and similarly with coil(s) 56. In operation, motive fluid in nozzles 60 will be preferably accelerated to supersonic velocities in converging/diverging nozzles 68, thereby entraining suction fluid from nozzles 11 in converging section 70 and final mixing section 72. The resulting high velocity mixture will then have such velocity converted to static pressure in diverging section 74 of eductor 16, which connects to transition nozzle 62 (which in turn connects to quench cooler 18).

EXAMPLE 1

2641 kg/hr of an LPG fresh feed at 620° C. enters a pyrolysis coil in admixture with 4859 kg/hr of recycle hydrocarbons and 4,200 kg/hr of steam. Hydrocarbon partial pressure at the inlet is 1.97 ata, and at the exit of the coil 1.36 ata, where the temperature is 830° C. The composition of the fresh feed is in weight percent about: ethane 2, propane 58, normal butane 20, isobutane 15, and pentanes 5. The ultimate weight percent yields of the product fractions are about: $H_2$&$CH_4$ 42.6, nonaromatics 6.0, light aromatics 34.4. and tar 17.0. Residence time in the pyrolysis coil 10 is about 0.60 seconds and the recycle ratio is 1.84. The total pressure of the stream in the pyrolysis coil 10 drops from about 4.34 ata at the entrance to about 2.5 ata at the exit. Neglecting subsequent pressure drops, "approximate horsepower" required to compress the gases therefrom to a separation pressure of 250 psia is about 830.

EXAMPLE 2

2500 kg/hr of propane at 620° C. and about 3.5 ata enters the pyrolysis coil 10, along with 1000 kg/hr of steam; and leaves the pyrolysis coil 10 at about 835° C. and about 2.0, after a residence time of about 0.5 seconds. Thereupon it is mixed with recycle gases also heated to a temperature of 835° C. After the residence time of 0.13 seconds, the mixture attains a temperature of 847° C., whereupon it is quenched. Ultimate weight percent yields of the product fractions are $H_2/CH_4$ 43.3, non-aromatics 14.7, light aromatics 33.4, and tar 8.6. Required recycle ratio is about 4.1, and "approximate horsepower" required is about 1900.

EXAMPLE 3

2500 kg/hr of propane at 620° C. and about 3.5 ata enters the pyrolysis coil 10, along with 1000 kg/hr of steam, and leaves the pyrolysis coil 10 at about 845° C. and about 2.0 ata, after a residence time of about 0.5 seconds. Thereupon it enters as suction flow to the eductor 16, with motive fluid consisting of recycle gases also heated to a temperature of about 845° C. at a pressure of about 6 ata. After a residence time of about 0.22 seconds in eductor 16, the mixture attains a temperature of about 908° C. (1666° F.), whereupon it is quenched. Ultimate weight percent yields of the product fractions are: $H_2/CH_4$ 46.8, non-aromatics 2.8, light aromatics 31.4, and tar 18.9. Required recycle ratio is about 1.2, pressure at the exit of the eductor is about 2.6 ata, and "approximate horsepower" is about 590.

Although in this specification the more preferred means of accomplishing the objects of the invention are described in detail, it will be clear to those skilled in the art involved that various substitute means may also be employed within the scope of the invention. Thus, the invention is not limited except as hereinafter stated in the claims.

We claim:

1. A process for the production of light aromatics from a feedstock comprising one or more of the natural gas liquid components which comprises:
   (1) pyrolyzing said feedstock in a first pyrolysis zone from a temperature of about 620° C. to a temperature in excess of about 750° C. for a total residence time less than about one second;
   (2) admixing the pyrolyzed feedstock with a pyrolyzed recycle stream comprising $C_2$-$C_4$ hydrocarbons such that the sensible heat of the admixture is sufficient to initiate the reaction of forming light aromatics;
   (3) quenching the reacting admixture;
   (4) separating said reacted admixture into a $C_{8+}$ tar and an offgas;
   (5) further separating the offgas into fractions comprising a light aromatic product and said recycle stream; and
   (6) pyrolyzing said recycle stream in a second pyrolysis zone to form the pyrolyzed recycle stream of step (2).

2. The process of claim 1, wherein said recycle stream is heated to in excess of about 750° C. during said second pyrolysis step.

3. The process of claim 2, wherein the total residence time of said recycle stream under pyrolysis conditions during said second pyrolysis step is less than about one second, thereby enhancing the yield of light aromatics relative to that of heavy aromatics.

4. The process of claim 1, wherein the pressure at the outlet of said second zone is greater than the pressure at the outlet of said first zone, thereby enhancing the yield of light aromatics and lowering subsequent compression requirements.

* * * * *